(12) United States Patent
Yang et al.

(10) Patent No.: US 7,226,884 B2
(45) Date of Patent: Jun. 5, 2007

(54) COMPOSITE FOR CATALYTIC DISTILLATION AND ITS PREPARATION

(75) Inventors: Yuanyi Yang, Beijing (CN); Dongfeng Li, Beijing (CN); Wei Dai, Beijing (CN); Shuo Chen, Beijing (CN); Guoqing Wang, Beijing (CN); Lihua Liao, Beijing (CN); Jianmin Cheng, Beijing (CN); Yanlai Guo, Beijing (CN); Hui Peng, Beijing (CN)

(73) Assignees: China Petroleum & Chemical Corporation, Beijing (CN); Sinopec Beijing Research Institute of Chemical Industry, Beijing (CN)

( * ) Notice: Subject to any disclaimer, the term of this patent is extended or adjusted under 35 U.S.C. 154(b) by 191 days.

(21) Appl. No.: 10/361,084

(22) Filed: Feb. 6, 2003

(65) Prior Publication Data
US 2003/0220187 A1 Nov. 27, 2003

(30) Foreign Application Priority Data
Feb. 7, 2002  (CN) ............................... 02 1 04203
Dec. 26, 2002 (CN) ............................... 02 1 56506

(51) Int. Cl.
*B01J 29/04* (2006.01)
(52) U.S. Cl. .................... 502/60; 502/325; 502/339
(58) Field of Classification Search ............... 502/325, 502/332, 333, 334, 335, 336, 337, 338, 339
See application file for complete search history.

(56) References Cited

U.S. PATENT DOCUMENTS 3,444,925 A * 5/1969 Johnson ..................... 165/166
3,856,706 A * 12/1974 Harrison et al. ............ 502/439
4,025,462 A * 5/1977 Cleveland .................. 502/300
4,122,039 A * 10/1978 Kobylinski et al. ........ 502/213
4,388,275 A * 6/1983 Fratzer et al. .............. 422/180
5,162,287 A * 11/1992 Yoshimoto et al. ........ 502/439
5,334,570 A * 8/1994 Beauseigneur et al. .... 502/304
5,336,651 A * 8/1994 Yoshimoto et al. .......... 502/74
5,422,331 A * 6/1995 Galligan et al. ............ 502/333
6,096,682 A * 8/2000 Steenackers et al. ....... 502/439
6,440,895 B1 * 8/2002 Tonkovich et al. ......... 502/439
6,559,094 B1 * 5/2003 Korotkikh et al. ......... 502/326
2002/0045541 A1* 4/2002 Koike et al. ............... 502/251

FOREIGN PATENT DOCUMENTS

WO    WO 01/17681    *  3/2005

* cited by examiner

Primary Examiner—Jonathan Johnson
(74) Attorney, Agent, or Firm—Birch, Stewart, Kolasch & Birch, LLP

(57) ABSTRACT

The present invention relates to a composite for catalytic distillation, comprising a substrate material, and a modifying material and an active material, wherein said substrate material is made of porous materials, said modified material comprises at least one metal oxide, and said active material comprises an active component for a catalytic reaction. The catalytic distillation composite according to the present invention serves as both distillation packings and catalysts, and can allow catalysts to make the best of its effenciency, provide sufficient contact areas between gas and liquid phases, which facilitates mass transfer between gas and liquid phases, boosts effects in both reaction and separation and is liable for filling, removing and utilizing in industries.

2 Claims, No Drawings

COMPOSITE FOR CATALYTIC DISTILLATION AND ITS PREPARATION

FIELD OF THE INVENTION

The present invention relates to a composite material for catalytic distillation useful in the fields of petrochemical industry, in particular, it relates to a composite material used for catalytic distillation columns in catalytic distillation processes, and the process for preparing the same.

BACKGROUND-ART

Catalytic distillation technology is a recently developed chemical engineering process, which combines catalytic step with distillation step, so that reactions and separations are carried out in the same column simultaneously. The process is capable of removing reaction products from each reaction-separation unit continuously and making use of reaction heat as the vaporization heat required for carrying out distillation. The catalytic distillation technology is characterized by higher conversions, better selectivity, less energy consumption, higher product purity, more convenient operation and less investments and so on, which has been widely researched and rapidly developed since the 80's. Such a technology first succeeded in the application for producing methyl t-butyl ether (MTBE) and then become widely used in many other areas.

A key to the catalytic distillation technology lies in the method by which the catalysts are filled into the reaction sections. Catalysts are filled in many ways which are generally divided into two types: one is a separate way, and the other is an integrated way. The process of the separate way produces catalysts and distillation packings separately, that is, catalysts are directly manufactured into granulates of various shapes and sizes, then combined with distillation packings by various means, and finally filled into distillation columns. For example, as described in U.S. Pat. No. 4,443,559 catalysts granules are filled in bulk into textile bags and supported by a stainless steel wired mesh covering having certain openings, which are rolled into cylindrical rolls consisting alternately of wired mesh layer and fabric bag's layer and form composite materials for use in distillation columns. According to another method of filling catalysts with packings in bulk disclosed in U.S. Pat. No. 5,262,012, granular catalysts are mixed with inert filling media such as ceramic balls, glass beads, hollow and porous balls or cylinders and then filled into columns. The major deficiency of the separate filling form lies in unevenly distributed catalysts in the bed, an excessive local pressure drop, poor gas/liquid flow, resulting in a non-uniform mixing, a non-uniform distribution in concentrations, and even undesirable dead corners. Moreover, design and fabrication of the composite are complex, the technical requirements are rigid, and filling and removal of packings are inconvenient, which are unfavorable to its application in the industry.

The process of integrated type combines catalysts and distillation packings as a whole to form an unitary and uniform element, and then put the element into a catalytic distillation column. For example, CN 1060228 describes a catalytic reaction-rectification column, wherein both trays or plates or packings in the column are directly formed by using active materials containing catalysts, which resolves problems of packing and filling of catalysts for catalytic rectification columns; however, the direct use of a catalytic active substances in forming the trays and packings leads to poor stength thereof, and further, elevated temperature and other factors during the production of trays and packings resulte in reduction or even lose of catalytic activity. In addition, the costs of both the trays and the packings are relatively higher.

Take futher examples, CN 1167009 discloses a mordenite/metal ceramic composite, which is prepared by incorporating an uniform layer of mordenite molecular sieve directly onto the surface of a metallic or ceramic substrate which is designed in advance and has an arbitrarily selected shape and size. CN 1228032 describes a catalytic packing useful in catalytic distillation process, which is prepared by vapor-depositing and/or spraying at least one active material as catalysts and/or promoters onto a substrate such as textiles, knitting or sheet-like packings. U.S. Pat. No. 5,235,102 discloses a catalytic distillation process for converting a feed stream in gas or liquid phase into desired products; one of the embodiment uses a rigid honeycomb ceramic block coated with catalytic active components as packings in a catalytic distillation column. In all the disclosed processes mentioned above, there always exist the problems: no matter on what a susbtrate, e.g. metals, ceramics, or textiles, the catalytic active coatings prepared by impregnation in liquids, vapor-depositing or spraying methods exhibit poor adhesion strength, which may peel off or be destructed, and thus damag the performances of catalysts. Accordingly, there still remains an urgent needs to improve the adhesion strength between a substrate and an active component layer.

DESCRIPTION OF THE INVENTION

It is an object of the present invention to provide a simple-to manufacture and ready-to-effect composite which can be used in catalytic distillation processes. The composite when used in catalytic distillation allows heterogeneous catalytic reactions and distillation or rectification to take place concurrently over it. This novel-type of catalytic distillation composite can bring catalytic action into full play, provide sufficient gas/liquid contact area, promote mass transfer between gas and liquid phases, obtain excellent effects in both reaction and separation, and is liable for filling, removing, and utilizing in industries.

AA composite used for catalytic distillation comprises a substrate material, a modifying material and an active material, wherein said substrate material is made off porous materials, said modified material comprises at least one metal oxide, and said active material comprises an active component for a catalytic reaction.

Preferably the said porous material is selected from porous metals or porous ceramics. Said modifying material is coated onto the surface of the substrate material, and said active material is loaded on the modified material, to form an uniform catalytic distillation composite providing functions of both reaction and distillation or separation.

The above substrate is a dumped packing or structured packing of porous metals or porous ceramics with any size or any shape.

In a catalytic distillation process, heterogeneous catalytic reactions take place concurrently with distillation or rectification over a catalytic distillation composite or catalyst packing, which thus requires not only that active components should be uniformly and strongly adhered to the substrate, have better adhesion strength, without peeling off, but also that such a composite or catalyst packing has an optimal material, shape and structure, in order that some components in the reaction mixture can be separated smoothly. Accordingly, the substrate of this invention preferably consists of a structured packing of porous metals or porous ceramics with any size or any shape which have a porosity ranging from 30 to 60% and a pore diameter from 0.1–20 μm, more preferably from 5 to 20 μm. For example, as the porous metal materials, it is prepared to use porous stainless steel materials and more preferably a composite of sintered micro-porous metal material. Aluminosilicate, high magnesium clays or diatomaceous earth and the like can be use as ceramics.

According to the present invention, the structured porous metal packing can be prepared by combining or assembling porous metal corrugated sheets. The structured porous ceramic packing can be formed by combining or assembling porous ceramic corrugated sheets, corrugated porous ceramic wired mesh, or porous ceramic fins.

Preferably, the porous metal corrugated sheets have pore diameter of 5–20 μm, porosity of 30–40%, thickness of 0.2–1.0 mm, corrugation angle of inclination of 30°–45°, and peak height and pitch of 5–30 mm respectively. Several pieces of corrugated metal sheet are combined into the structured porous metal packing. Preferably, said structured porous metal packing is formed into an integrated structure, having the shape of disc when the diameter is smaller than 500 mm, having 6 sections to be pieced together when the diameter is smaller than 800 mm, and having 9 sections or more to be pieced together when the diameter is larger than 800 mm.

The porous ceramic corrugated sheet, porous ceramic wired mesh or porous ceramic fin which forms the structured porous ceramic packing of the present invention can be manufactured by a conventional method, and is preferably manufactured by the process comprising the following steps, (1) 60–80 wt % off substrate, 20%–40 wt % distilled water together with 10%–20 wt % binder and pore-forming agent are mixed up and ball-milled for 5–20 hour to form a homogeneously dispersed slurry which is then adjusted to pH5.0–7.0; (2) the slurry obtained in step (1) is extrusion formed by means of a predetermined die, for a preferred corrugated porous ceramic sheet, the die should meet the requirement of peak height, pitch and angle of inclination; the preform thus obtained is trimmed to make the packing have a smooth surface without defects thereon, and dried at ambient temperature, and is opened several holes; (3) the dried preforms are assembled in such a way that waves or corrugations in two adjacent corrugated sheets are perpendicular to each other, and the contacting peaks there-be-tween are bound with the binder to form a complete disc or tray; (4) the assembled packing is sintered in an oven at 800–1000° C., to obtain the structured porous ceramic packing, wherein, in step (1), starch is preferably used as the binder and pore-forming agent, and HCl or tetramethyl ammonium hydroxide is preferably used to adjust Ph of the slurry; and in step (3), water glass is preferaby used as the binder. Preferably, said structured porous ceramic packing is formed into integrated tray if a diameter of smaller than 500 mm required, or is formed by 6 sections to be pieced together if a diameter of smaller than 800 mm is required, or by 9 sections or more to be pieced togrther if a diameter of larger than 800 mm is required.

Preferably, the structured porous ceramic packings consist of the porous ceranic corrugated sheets, which have an uniform microporous structure, a porosity of 30–60%, a pore diameter of 10–18 μm, a wall thickness between 0.8 and 1.2 mm, corrugation angle of inclination of 30°–45°, peak height and pitch of 5–30 mm respectively, and holes or openings of 3–6 mm in the wall of corrugated sheets for the purpose of improving mass transfer.

For achieving better separation effects during catalytic distillation, the substrate according to the present invention preferably has a specific surface area greater than 400 $m^2/m^3$, more preferably 400–800 $m^2/m^3$ and a void ratio of 70–95%, preferably greater than 90%, and the number of theoretical, column trays of more than 4 per meter.

It is worth noting that the substrate used in present invention is modified by surface-treatment, in particular, the substrate is treated with a modifying material comprising useful metal oxides to form a coating layer comprising the modifying material, in order that the catalytic active materials can be attached to the substrated efficiently and firmly. Said metal oxides are selected from the group consisting of $Al_2O_3$, $SiO_2$ or $TiO_2$. Alumina is preferred, which has several variants. Having stable structure, $\alpha$-$Al_2O_3$ is preferred for the purpose of the active components to be loaded on the substrate used for the composite for catalytic distillation according to the present invention. Generally, the multiple variants of $Al_2O_3$ will be transformed into $\alpha$-$Al_2O_3$ when treated to 1100° C. or above. It is the calcinating temperature that decides the morphology of $Al_2O_3$. For example, $\gamma$-$Al_2O_3$ is generally obtained when the calcination temperature ranges from 400 to 600° C., $\alpha$-$Al_2O_3$ when the calcination temperature ranges from 1000 to 1200° C.

The performances of the modifying material also depend on particle size of the modifying material, generally, an average particle size is controlled within 10 μm, preferably below 1 μm.

The substrate is coated with the modifying material by a thermo-chemical reaction process comprising the following steps:

a) preparing a water-based coating material in which superfine particles with particle size below 10 μm of the modifying material are dispersed, wherein the ratio of modified material to water is in a range between 1:2 and 1:5 and pH of the solution is adjusted to a range between 2 and 4;

b) coating the substrate material with the water-based coating material obtained from step a), the obtained substrate material is subjected to drying and curing treatment to form a modified coat on the surfaces of the substrate material.

Preferably, the said process comprises the steps of 1) preparing a water-based coating by using superfine particles selected from alumina, silica or titania of particle size below 10 μm, adding distilled water with a weight ratio of 1:2–1:5 and stirring until homogeneous, adding phosphorous acid to adjust Ph of the solution to 2–4, to form a water-based coating material; cleaning and drying the surface of the substrate;

2) dip-coating the substrate with the water-based material to form a uniform coat, and drying at ambient temperature;

3) drying the obtained substrate at 100–120° C.;

4) calcinating the dried substrate at 600–800° C. for 6–12 hours to carry out curing treatment so as to accelerate chemical reactions and finally to obtain a layer of uniform and stabilized ceramic coating. During the curing process, oxides on the surface of substrate and in coatings have thermo-chemical reactions to form a compound phase whereby the coat and metal substrate are firmly bound together.

The active components in the composite of the present invention are selected from the group consisting of metals of group VIII or IB, or a mixture thereof, or selected from an acid cation exchange resin or a zeolite molecular sieve of Y, X, β-and various modified types. Metals used as the active components in present invention include elements selected from copper, silver, gold, rhenium, ruthenium, cobalt, rhodium, nickel, palladium, platinum and a mixture thereof.

In general, these catalytic active components will be evenly coated on a structured porous metal packings having modifying materials. After the substrate is coated with modifying material, catalytic active components can uniformly and firmly applied onto the modifying material of a pre-tailored structured porous metal or ceramic packings by a dip or spray process to form an active layer thereon, and the composite for catalytic distillations of the present invention is thus obtained.

The present invention provides two methods for forming an active layer, one of which is liquid phase immersion method and the other is a spray method.

Said liquid phase immersion is carried out by immersing modified structured porous metal packings in a solution comprising catalytic active components, the packings are removed from the solution after crystallization for a period of 24 to 48 hours, washed and dried. Said operation is repeated several times and followed by baking at 400–600° C. for 8–12 hours to obtain a catalytic distillation composite having both reaction and distillation or separation functions.

Said spray method is effected by spraying with a prepared catalytic active components-containing solution onto a modified structured porous metal packing by means of a sprayer, drying it at 50–150° C., and baking it at 400–600° C. for 8–20 hours, and then reducing it under a reductive gas such as hydrogen for 1.0–1.2 hours to obtain said catalytic distillation composite.

The composite of present invention is useful for many chemical processes in catalytic distillation field, including, for example, processes of catalytic distillation-selective hydrogenation of cracking gas, esherification, ether-splitting, esterification, alkylation, isomerization, dehydration, and hydrolysis and so on.

The catalytic distillation composite of present invention exibits the following advantages:

1) Attributed to the combination of the substrate, modifying material and active components, the composite functions as both distillation packing and catalyst, which provides good performances of separation and reaction, makes catalytic distillation operation going on smoothly and increases conversion rate and selectivity of catalytic reactions;

2) Comprising a structured porous metal packing as substrate, the catalytic distillation composite exibits the nature of metals such as excellent heat transfer, sufficient strength and toughness. Further, the composite can be manufactured and installed in a convenient way;

3) Having a ceramic coat as a modifying material on the substrate after surface-treatment, the composite has catalytic active components to be firmly adhered to the substrate and thus avoids lose of active components;

4) Uniform distribution of catalytic active components in the composite enlarges geographic area of the catalyst so that the catalysts can be utilized more efficiently;

5) The shape and size of the composite is flexible and can be adjusted in accordance with needs or requirements. The same is for active components and their proportions;

6) The composite provides larger porosity and specific area, a reduced pressure drop and much increased mass and heat transfer efficiencies.

Preferred Embodiments

EXAMPLE 1

A porous metal sheet of stainless steel substrate (provided by An-Tai Technology Co. Limited, Chinese Academy of Iron and Steel Research) having uniform microporous structure, pore diameter of 10–20 µm, a porosity of 35% and a wall thickness of 0.5 mm was adopted. The porous metal sheets were fabricated into corrugated sheets having corrugation angle inclination of 45° and both peak height and pitch of 15 mm by a conventional method for forming corrugated metal sheets. Several corrugated metal sheets obtained according to the method mentioned above were assembled together wherein two adjacent corrugated sheets were perpendicular to each other, to form a structured packing tray of ϕ100×=mm.

EXAMPLE 2

A structured porous metal packing manufactured in Example 1 was subject to surface-modification. (1) Superfine alumina powder having particle size of below 10 µm was adopted, distilled water was added in a weight ratio of 1:3 (alumina: water) and the whole was agitated until homogeneous, phosphorous acid was then added to adjust pH of the solution to 2.5 and whereby a water-based coating material was prepared; (2) the structured porous metal packing was surface cleaned and dried; (3) the structured porous metal packing was evenly coated with the water-based coating material, and dried in air at ambient temperature; (4) the structured porous metal packing was baked in an oven at 110° C. ; (5) the dried structured porous metal packing was subject to heat treatment for curing by being baked at 600° C. for 8 hours, to obtain a modified structured porous metal packing.

EXAMPLE 3

The catalytic distillation composite according to present invention was used in the preparation of ethylbenzene by alkylation of benzene and ethylene. The modified structured porous metal packing prepared in Example 2 was loaded with P-zeolite by the liquid phase immersion process. β-zeolite with particle size of below 10 µm was used, to which distilled was added in a weight ratio of 1:2 (zeolite:water), and the whole was stirred until homogeneous, nitric acid was then added to adjust pH of the resulting solution to 4, the structured porous metal packing was then dipped in the solution for 48 hours and removed therefrom for washing, drying, and crystallizing; and the above procedure of dipping, washing, drying, and crystallizing was repeated thrice; the thus obtained material was baked at 500° C. for 10 hours to form a porous metal composite for catalytic distillation. The catalytic distillation composite was then installed in a reaction section of a ϕ100 mm catalytic distillation column comprising a reaction section of 2 m high and a stripping section of 6 m high wherein the latter section was randomly filled with the packings of ϕ6×6 mm cannon stainless steel rings with openings. The operation conditions were: space velocity (by weight) for ethylene of 0.28 $h^{-1}$, benzene/ethylene molar ratio of 6:1, and system pressure of 1.8 MPa, and reaction temperature between 150 and 180° C. Under these conditions, a good result was obtained with the ethylene conversion of 100% and the average selectivity for ethylbenzene of 98%.

EXAMPLE 4

The catalytic distillation composite according to present invention was used in the preparation of isopropyl benzene from propylene and benzene through alkylation. The catalytic distillation composite was prepared according to the process described in Example 1–3, except that the porous metal corrugated sheets were formed into those having a peak height of 15 mm, pitch of 30 mm, corrugation angle of inclination of 30° and wall thickness of 0.5 mm and further into a $\phi$500×200 mm structured porous metal packing tray. The obtained catalytic distillation composite was then installed in a reaction section of a $\phi$500 mm catalytic distillation column comprising a reaction section and a stripping section wherein the reaction section was 9 m high, and the stripping section was 3 m high and was filled with the structured metal packing of type 250Y($\phi$500×200 mm). Operation conditions were: space velocity ( by weight) for propylene of 0.36 $h^{-1}$, benzene/propylene molar ratio of 6:1, and system pressure of 0.8 MPa, and reaction temperature between 140 and 180° C. Under these conditions, the propylene conversion of 100% and the average selectivity for isopropyl benzene of 98% were achieved.

EXAMPLE 5

The catalytic distillation composite according to present invention was used in a catalytic distillation-selective hydrogenation of a $C_3$ fraction for removing methylacetylene and propadiene (MAPD). The modified structured porous metal packing fabricated in example 2 was loaded with catalytic active component Pd by spray coating. A solution of palladium chloride or palladium nitrate, comprising 0.5 wt % Pd, was formulated adjusted to pH5.0–6.5. The resulting solution was sprayed onto a modified substrate previously heated to 40–60° C. by using a suitable sprayer and followed by drying at 120° C. The packing loaded with Pd was baked at 350–500° C., preferably not exceeding 500° C., for 10 hour in general, and then treated in a hydrogen gas under an appropriate pressure and a temperature from 60 to 120° C. for a period of 12 hours for reduction, so as to obtain the catalytic distillation porous composite. The hicomposite was installed in a reaction section of a $\phi$100 mm catalytic distillation column with 6 m high comprising a fraction section, a reaction section and a stripping section wherein the reaction section measured 1 m high into which 20 pieces of $\phi$100×50 mm catalytic distillation composite obtained above were installed, and the rectification and stripping sections each were 5 m high into which $\phi$6×6 mm cannon stainless steel rings with openings were randomly filled. The raw materials were fed from the lower part of the reaction section and products came out from the top. The feed had the following composition.

| components | $C_2°$ | $C_3°$ | $C_3^-$ | $C_3^{--}$ | $C_3^=$ | $C_4$ | $C_5$ |
|---|---|---|---|---|---|---|---|
| Molar fraction (2) | 0.02 | 2.50 | 72.14 | 1.08 | 2.09 | 19.43 | 2.72 |

A test was conducted under conditions of reaction temperature of 40–50° C., reaction pressure of 1.6–1.8 MPa, space velocity by volume of liquid phase feed of 2 $h^{-1}$ and a ratio between hydrogen and alkyne of 1.1. Results of the test show that the catalytic distillation composite has good performances in both reaction and distillation or separation, as evidenced by the fact that contents of both methylacetylene and propadiene have been lowered to below 3 ppm and the yield of propylene is up to 103% after catalytic distillation.

EXAMPLE 6

A mixture of 70 wt % of $Al_2O_3$ and 20 wt % of distilled water was mixed and 10 wt % of starch was added therein. After the mixture was mixed in a ball mill for 6 hours, a uniformly dispersed slurry was formed and was then adjusted to pH6 with HC1. The slurry was extrusion molded by using a designed mold into corrugated sheets (preform) having peak height of 6 mm, pitch of 12 mm, corrugation angle of 45°, wall thickness of 0.8 mm and openings of $\phi$4mm in the wall. The obtained preform was, after trimming, dried in air at ambient temperature, then each dried sheet was assembled together, wherein two adjacent sheets were perpendicular to each other and the peaks were bound with water glass to form a finished structured packing tray of $\phi$100×100 mm. The assembled packing trays were baked in an oven at 800–900° C. to obtain structured packings used as the substrate.

EXAMPLE 7

A structured porous ceramic packing fabricated in Example 6 as a substrate was surface-modified by immersing a $\phi$100×100 mm structured porous ceramic packing tray in a suspension of aluminum hydroxide for 20 hours, taking out, and baking at 1100° C. for 12 hours, during which the thin coating layer comprising alumina hydrate underwent a phase conversion to obtain a a-type alumina. The substrate which was surface-modified with ($\alpha$-$Al_2O_3$) had a specific area of 550 $m^2/M_3$.

EXAMPLE 8

A hydrogenation catalyst was prepared by coating the substrate comprising a modifying layer formed in Example 7 with a Pd-containing solution. An aqueous solution of palladium chloride or palladium nitrate containing 0.5 wt % of Pd was prepared, adjusted to a pH between 5.0–6.5, sprayed onto a modified substrate preheated to 40–60° C., and then dried at 120° C. The Pd-loaded packing was baked at 350–500° C., preferably not exceeding 500° C., for 10 hours in general, and then treated in a hydrogen gas under an appropriate pressure and temperature from 60 to 120° C. for 12 hours for reducing the catalyst, to obtain catalytic active component-containing packings.

EXAMPLE 9

The structured member obtained in Example 8 for use in a catalytic distillation column was installed in the reaction section of a $\phi$100 catalytic distillation column. In the column, a test of catalytic distillation for hydrogenation of a $C_3$ fraction was conducted though selective hydrogenation and removal of methylacetylene and propadiene contained in propylene. The catalytic distillation column was 6 meters high and consisted of a rectification section, a reaction section and a stripping section, wherein the reaction section was 1 meter high in which 10 pieces of $\phi$×100×100 mm structured porous packing trays were installed, and the rectification and stripping sections were 5 meters high which were filled with dumped packings of φ6×6 mm cannon stainless steel rings with openings. Raw materials were fed from the lower part of the reaction section and products came out from the top. The results of test are shown in Table 1 below.

TABLE 1

| Location | | feed | Tops | botoms |
|---|---|---|---|---|
| Composition | $C_2°$ | 0.02 | 0.02 | |
| mol % | $C_3°$ | 2.50 | 4.11 | 1.46 |
| | $C_3^-$ | 72.14 | 95.87 | 11.29 |
| | $C_3^{--}$ | 1.08 | 4 ppm | 2.47 |
| | $C_3^=$ | 2.09 | 3 ppm | 4.72 |
| | $C_4°$ | 19.43 | | 74.05 |
| | $C_5°$ | 2.72 | | 6.02 |
| flow (l/h) | | 10 | 7.4 | 2.6 |
| temperature (° C.) | | 25 | 42 | 98 |
| pressure (MPa) | | 2.3 | 1.75 | 1.78 |
| H/alkyne | | | 0.9 | |
| Propylene yield (%) | | | 101.9 | |

It can be seen from the results of the test that the structured member for catalytic distillation of the present invention has a good performances in both reaction and separation as evidenced by the fact that contents in both methylacetylene and propadiene in the overhead products have been lowered to below 3 ppm after catalytic distillation.

EXAMPLE 10

The performances of the structured members for catalytic distillation that had been surface-modified with different types of $Al_2O_3$ were compared. Multiple φ100×1.00 mm structured porous packings fabricated in Example 6 were immersed in a suspension containing aluminum hydroxide for 20 hours, taken out, and divided into two groups and baked for 12 hours at 500° C. and 1100° C. respectively, which result in that packings were surface modified with γ-$Al_2O_3$ or α-$Al_2O_3$ accordingly. After modification, the modified structured porous ceramic packings were coated with metal Pd in the same manner as indicated in Example 3. The two groups of structured catalytic distillation members were placed in a reaction section of catalytic distillation column separately in the similar manner as mdicated in Example 4 and tested in separate runs of catalytic distillation for hydrogenation of $C_3$ fraction under conditions given in Example 4. The results are shown in table 2.

TABLE 2

| structured member for catalytic distillation | γ-$Al_2O_3$ modified | α-$Al_2O_3$ modified |
|---|---|---|
| specific area ($M^2$/g) | 50 | 10 |
| convesion (%) | 99.98 | 99.96 |
| selectivity (%) | 46.38 | 82.44 |

It can be seen from the results that the structured members used in a catalytic distillation column modified with α-$Al_2O_3$ have both higher conversion and better selectivity while those structured members used in a catalytic distillation column modified with γ-$Al_2O_3$ have a high conversion but a poorer selectivity. Thus, according to the present invention, using α-$Al_2O_3$ to modify the surface of structured porous ceramic packing for a catalytic distillation column shows better result.

The invention claimed is:

1. A method for preparing a composite for catalytic distillation comprising a substrate material, a modifying material and an active material, said substrate material comprising structured packing made up of porous metals or porous ceramic materials, said modifying material comprises at least one metal oxide, and said active material comprises an active component for a catalytic reaction, the method comprising the steps of:
   (1) coating a surface of the substrate material with the modifying material by using a thermo-chemical reaction process, which comprises the steps of:
      a) preparing a water-based coating material in which superfine particles with particle size below 10 μm of the modifying material are dispersed in a solution, wherein a ratio of modifying material to water is in a range between 1:2 and 1:5, and a pH of the solution is adjusted to a range between 2 and 4, and
      b) coating the substrate material with the water-based coating material obtained from step a), and the obtained substrate material is subjected to drying and curing treatment to form a modified coat on the surfaces of the substrate material; and
   (2) loading the active material containing active components onto the modifying material by using a dip-or spray-coating process.

2. The method according to claim 1, wherein said substrate has a specific area greater than 400 $m^2/m^3$ and a voidage of 70–95%.

* * * * *